US012564478B2

(12) United States Patent
Salah et al.

(10) Patent No.: US 12,564,478 B2
(45) Date of Patent: Mar. 3, 2026

(54) METHOD FOR ANALYSING A DENTAL SITUATION

(71) Applicant: DENTAL MONITORING, Paris (FR)

(72) Inventors: Philippe Salah, Paris (FR); Thomas Pellissard, Clichy (FR); Guillaume Ghyselinck, Cantin (FR); Laurent Debraux, Paris (FR)

(73) Assignee: DENTAL MONITORING, Paris (FR)

( * ) Notice: Subject to any disclaimer, the term of this patent is extended or adjusted under 35 U.S.C. 154(b) by 919 days.

(21) Appl. No.: 17/057,608

(22) PCT Filed: May 14, 2019

(86) PCT No.: PCT/EP2019/062380
§ 371 (c)(1),
(2) Date: Jan. 13, 2021

(87) PCT Pub. No.: WO2019/224055
PCT Pub. Date: Nov. 28, 2019

(65) Prior Publication Data
US 2021/0186658 A1 Jun. 24, 2021

(30) Foreign Application Priority Data
May 22, 2018 (EP) .................................... 18305627

(51) Int. Cl.
*A61C 7/00* (2006.01)
*A61B 90/00* (2016.01)
(Continued)

(52) U.S. Cl.
CPC .............. *A61C 7/002* (2013.01); *A61B 90/36* (2016.02); *A61C 7/08* (2013.01); *A61C 9/0053* (2013.01);
(Continued)

(58) Field of Classification Search
CPC ....... A61C 7/002; G06T 7/0014; G06T 11/00; G06T 2200/24; G06T 2207/30036
See application file for complete search history.

(56) References Cited

U.S. PATENT DOCUMENTS 10,467,815 B2 * 11/2019 Marom .................. A61B 34/10
2002/0064747 A1 5/2002 Chishti et al.
(Continued)

FOREIGN PATENT DOCUMENTS

CN 105832291 A 8/2016
WO WO 2016/066651 A1 * 5/2016 .......... C07D 471/04
WO 2017182648 A1 10/2017

OTHER PUBLICATIONS

Monitoring of Tooth Movement, Philippe Sa/ah and K. Hero Breuning Digital Planning and Custom Orthodontic Treatment, First Edition. 2017 John Wiley & Sons, Inc. Published 2017 by John Wiley & Sons, Inc. (Year: 2017).*

(Continued)

*Primary Examiner* — Chuen-Meei Gan
(74) *Attorney, Agent, or Firm* — Ronald M. Kachmarik; Cooper Legal Group LLC

(57) ABSTRACT

A method for analyzing a real dental situation of a patient. The method includes steps, as follows, in succession. At an updated instant, acquisition of an updated image representing a real dental scene as observed by an operator. Simulation, for a simulation instant, of the real dental scene represented on the updated image, then determination of a virtual dental scene as a function of the simulation. Presentation of the virtual dental scene in transparent mode and overlaid on the real dental scene, or display of the updated image on a screen and presentation of the virtual dental scene overlaid with the representation of the real dental (Continued)

scene on the updated image displayed on the screen, in transparent mode or not on the representation.

12 Claims, 3 Drawing Sheets

(51) Int. Cl.

| | |
|---|---|
| *A61C 7/08* | (2006.01) |
| *A61C 9/00* | (2006.01) |
| *G06T 7/00* | (2017.01) |
| *G06T 11/00* | (2006.01) |

(52) U.S. Cl.
CPC ............ *G06T 7/0014* (2013.01); *G06T 11/00* (2013.01); *A61B 2090/365* (2016.02); *G06T 2200/24* (2013.01); *G06T 2207/30036* (2013.01)

(56) References Cited

U.S. PATENT DOCUMENTS

| | | |
|---|---|---|
| 2004/0197727 A1 | 10/2004 | Sachdeva et al. |
| 2006/0115793 A1 | 6/2006 | Kopelman et al. |
| 2014/0379356 A1 | 12/2014 | Sachdeva et al. |
| 2017/0325910 A1 | 11/2017 | Salah et al. |
| 2018/0055600 A1 | 3/2018 | Matov et al. |

OTHER PUBLICATIONS

International Search Report corresponding to International Application No. PCT/EP2019/062380 dated Aug. 19, 2019, 7 pages.
Chinese Office Action from Corresponding Chinese Patent Application No. 202310350199.X, dated Jul. 11, 2025.

* cited by examiner

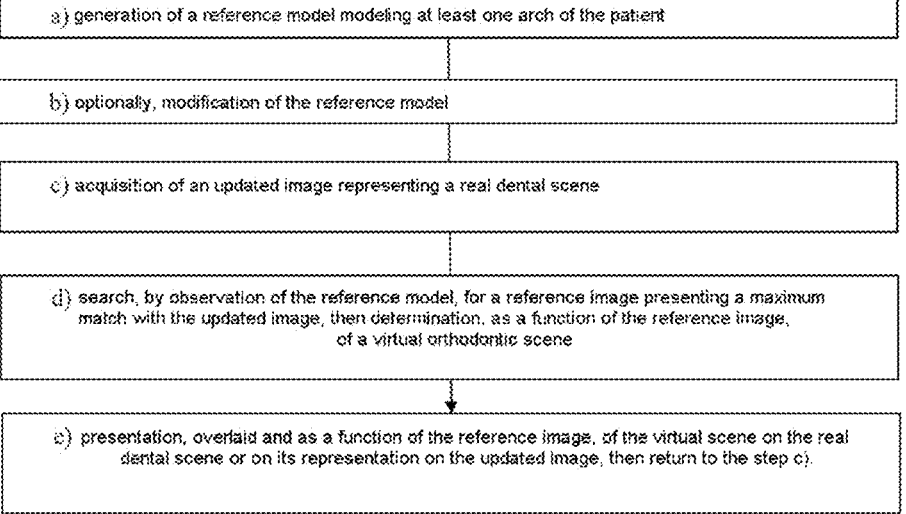

a) generation of a reference model modeling at least one arch of the patient b) optionally, modification of the reference model c) acquisition of an updated image representing a real dental scene d) search, by observation of the reference model, for a reference image presenting a maximum match with the updated image, then determination, as a function of the reference image, of a virtual orthodontic scene e) presentation, overlaid and as a function of the reference image, of the virtual scene on the real dental scene or on its representation on the updated image, then return to the step c).

Fig. 1

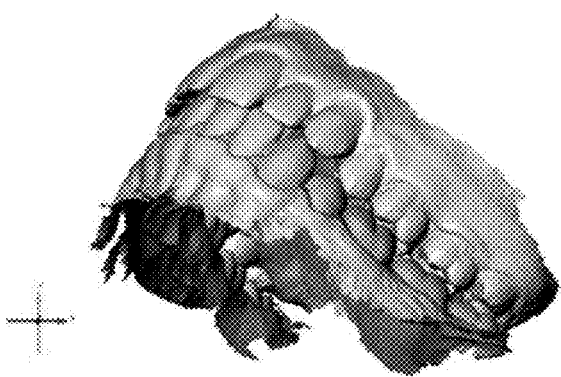

Fig. 2

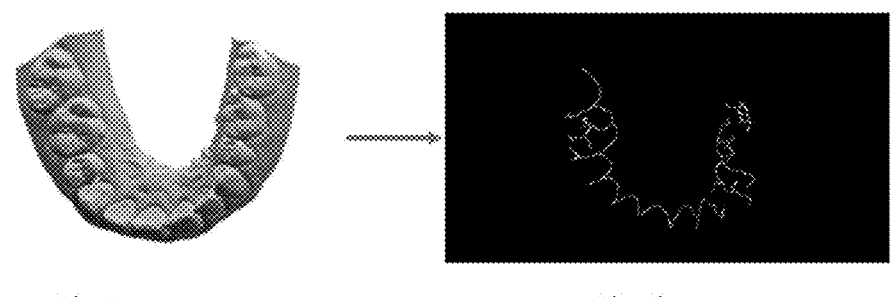
Fig. 3a                                        Fig. 3b
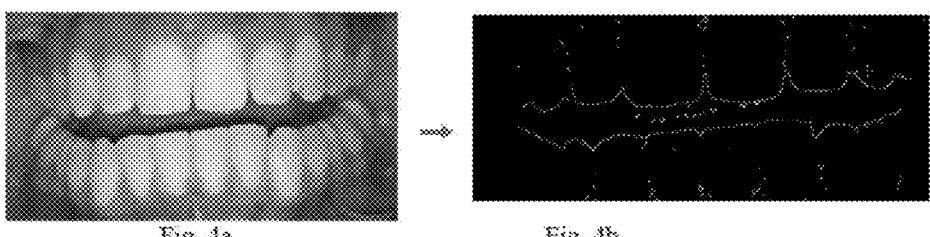
Fig. 4a                                        Fig. 4b
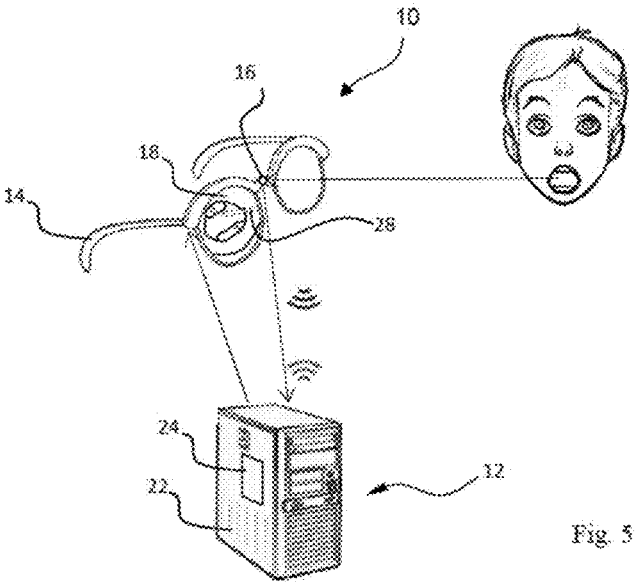
Fig. 5

METHOD FOR ANALYSING A DENTAL SITUATION

TECHNICAL FIELD

The present invention relates to the analysis of a dental situation of a patient.

STATE OF THE ART

When a dental care professional intervenes on the teeth of a patient or performs a diagnosis, he or she needs to assess the real dental situation, and in particular the position and/or the form and/or the dimensions of the teeth and/or the good positioning of an orthodontic appliance fixed to the teeth.

This assessment generally requires a comparison of the real dental situation with a theoretical dental situation. For example, to diagnose the detachment of an attachment of an orthodontic appliance, it may be necessary to compare the real dental situation in which the attachment is abnormally separated from the tooth to which it is supposed to be glued, with a theoretical dental situation in which said attachment is actually glued to said tooth. This need exists notably in individualized treatments, for which the attachments are shaped to be adapted precisely to the morphology of the teeth and/or according to the specific prescriptions of the dental care professional.

The dental care professional also performs a comparison between a theoretical dental situation and a real dental situation when seeking to assess whether a tooth is abnormally positioned or exhibits an abnormal form. The real position or form or dimension of the tooth must in particular be compared with a theoretical position or form or dimension that the tooth should exhibit at the moment of comparison by the dental care professional.

Moreover, the analysis of the real dental situation sometimes needs to be performed very rapidly, even in real time. For example, when the dental care professional intervenes by means of a tool to modify the form or the appearance of a tooth, the action that he or she exercises on the tool has to be precise and be adapted in an ongoing manner to a real dental situation which changes.

Generally, the quality of the comparison between the real dental situation and the theoretical dental situation has an impact on the quality of the treatment, whether it be therapeutic or not.

There is therefore an ongoing need for an analysis method that allows the appreciation of a real dental situation, notably by a dental care professional, to be improved.

Moreover, the effectiveness of a dental treatment is directly linked to the compliance by the patient with the medical prescription. Failing good observance, the dental situation can worsen, which leads to an additional risk for the patient, but also costs for Social Security or care financing organizations.

Poor observance of a treatment also makes clinical studies more difficult, particularly if the patient does not declare the periods of nonobservance.

There is therefore a need for a method that allows the observance to be improved.

One aim of the invention is to at least partially address these needs.

SUMMARY OF THE INVENTION

The invention proposes a method for analyzing a real dental situation of a patient, the method comprising the following successive steps:

A) at an updated instant, acquisition, preferably by means of a camera, of an updated image representing a real dental scene;

B) determination of a virtual dental scene as a function of the representation of the real dental scene on the updated image;

C) presentation of the virtual dental scene in transparent mode and overlaid on the real dental scene, in particular on a screen through which the real dental scene is visible or projected onto the real dental scene, or overlaid with the representation of the real dental scene on the updated image displayed on a screen, in transparent mode or not on said representation, then, preferably, return to the step A).

In a particular embodiment, the step B) consists of a simulation, for a simulation instant, of the real dental scene represented on the updated image, then of a determination of a virtual dental scene as a function of said simulation.

As will be seen in more detail hereinafter in the description, a method according to the invention therefore allows the operator to simultaneously observe the real dental scene, directly or through a screen on the one hand, or on the updated image on the other hand, and the virtual dental scene, overlaid with the real dental scene or with the representation of the real dental scene on the updated image, respectively.

This overlay considerably facilitates the analysis, by the operator, preferably in real time, of the differences between the real dental scene and the virtual dental scene. It also allows for the addition of information relating to the real dental scene and for that information to be arranged according to the representation of the real dental scene on the updated image. The quality of the transmission of that information to the operator is thereby enhanced. Finally, it allows for a realistic simulation of a dental situation, for example a simulation of an esthetic treatment.

When the method is implemented by a dental care professional, it allows him or her to improve the quality of his or her intervention on the patient. When it is implemented by the patient in particular, it makes it possible to realistically simulate the effect of a dental treatment or of a modification of a dental treatment, which improves the observance thereof.

A method according to the invention can also comprise one or more of the following optional features:

in the step B), the virtual dental scene comprises the representation of one or more physical elements of the real dental scene modeled by the reference model, and/or the representation of one or more physical elements of the real dental scene not modeled by the reference model, and/or the representation of one or more physical elements which are not in the real dental scene and/or which are not in the reference model, and/or an indicator which does not represent a physical element of the real dental scene, preferably several such indicators;

in the step B), an element of the virtual dental scene is identified which does not comply with an assessment criterion, and this element is highlighted in the virtual dental scene and/or a message relating to said element is added to the virtual dental scene;

the assessment criterion relates to the state of health of the patient and/or to the positioning of an orthodontic appliance worn by the patient and/or to the condition of an orthodontic appliance worn by the patient and/or to a cost for a dental treatment;

the message is an instruction to be followed by the patient and/or by a dental care professional responsible for the patient;

in the step B), the nature and/or the location and/or the appearance of an element of the virtual dental scene, and notably of an indicator, is determined as a function:

of the context, and in particular as a function of the distance to another element of the virtual dental scene and/or as a function of a pursued objective;

in the step B), the nature and/or the location and/or the appearance of elements of the virtual dental scene are determined as a function of the nature and/or of the location and/or of the appearance of elements displayed in prior virtual dental scenes, that is to say from prior cycles of steps A) to C), and/or as a function of the time interval with said prior virtual dental scenes, and/or as a function of differences between the updated images of successive cycles of the steps A) to C);

in the step B), the virtual dental scene is determined in such a way that it comprises information, notably textual or graphic, on differences between the updated image and the reference image, and/or differences between the reference model and the real dental scene, and/or a target location, notably for a tool or an orthodontic appliance or a decorative item;

in the step C), the virtual dental scene is presented on the real dental scene or on the updated image so that the representations of real physical elements of the virtual dental scene are overlaid, realistically, with said real physical elements or with the representations of said real physical elements on the updated image, respectively;

a step A) is repeated less than 5 seconds after the step C), respectively;

after the step C), an orthodontic appliance is modified and/or the arch is adjusted and/or an item or an orthodontic appliance is positioned as a function of the presentation of the virtual dental scene on the real dental scene or on the representation of the dental scene on the updated image.

According to an aspect of the invention, in the step C), the virtual dental scene is presented on a transparent screen, overlaid with the real dental scene that an operator can observe through the screen, in particular when facing the screen.

Preferably, the screen and the camera are immobilized with respect to the operator. Preferably, they are incorporated in glasses. The method according to the invention is then particularly useful for a dental care professional wearing the glasses to be able to assess, in real time, the dental situation of a patient that he or she is examining.

Notably according to this aspect of the invention, a method according to the invention can be used to assess, in real time, a stripping or milling operation, or an operation for positioning an orthodontic appliance or a part of an orthodontic appliance.

According to an aspect of the invention, in the step C), the virtual dental scene is presented, overlaid with the representation of the real dental scene on the updated image, on an opaque screen, that is to say through which the operator cannot see.

In one embodiment, the screen is that of a cellphone, of a tablet, of a laptop computer, or of a virtual reality headset. The screen can also be the glass of a mirror, preferably equipped with at least one camera.

Preferably, the operator manipulates a cellphone, a laptop computer, a virtual reality headset or a mirror equipped with at least one camera, to acquire said updated image and view the real dental scene and the virtual dental scene.

According to this embodiment, the dental care professional can work on the arch of the patient by watching the screen. He or she then sees, simultaneously on the screen, the images acquired by the camera and the information supplied by the virtual dental scene. He or she can in particular work "blind" (that is to say without seeing, directly or through a screen, the real dental scene), on regions of the arch that he or she cannot observe directly but that can be observed by the camera, notably when the camera is independent of the screen and, in particular, when the camera can be introduced into the mouth of the patient.

In one embodiment, in the step B) or d), the virtual dental scene is determined as a function of a value of at least one treatment parameter that can be modified by interaction with said cellphone, said laptop computer, said virtual reality headset, said camera, said mirror or said glasses, preferably with the cellphone. Preferably, the treatment parameter relates to the wearing of an orthodontic appliance by the patient and/or to the observance of a treatment instruction by the patient.

A method according to the invention, notably according to this aspect of the invention, can facilitate the decision-making by the patient, in particular because it allows him or her, by choosing the simulation instant, to view the effect, on his or her appearance, of the possible different treatment options. The method can also be an efficient teaching tool to improve observance.

Use of a Reference Model

In a preferred embodiment, the virtual dental scene is determined by means of a three-dimensional digital model digitally modeling at least one arch of the patient, called "reference model".

Preferably, the reference model is used also, in the step C), to position the virtual dental scene with respect to the real dental scene or the representation thereof.

Advantageously, the composition of the virtual dental scene can thus be entirely automated.

The method according to the invention can in particular comprise the following successive steps:

a) at a reference instant, generation, preferably by means of a scanner, of a reference model digitally modeling at least one dental arch of the patient;

b) optionally, modification of the reference model;

c) at an updated instant, acquisition, preferably by means of a camera, of an updated image representing a real dental scene;

d) search, by observation of the reference model, optionally modified, for a reference image presenting a maximum match with the updated image, then determination, as a function of the reference image, of a virtual dental scene;

e) presentation of the virtual dental scene in transparent mode and overlaid on the real dental scene, in particular on a screen through which the real dental scene is visible or projected onto the real dental scene, or overlaid with the representation of the real dental scene on the updated image displayed on a screen, in transparent mode or not on said representation, then, preferably, return to the step c).

The step c) is a particular case of step A). The optional features applicable to the step A) are therefore applicable to the step c).

The steps a), b) and d) constitute together a particular case of step B). The optional features applicable to the step B) are therefore applicable to the steps a), b) and d).

The step e) is a particular case of step C). The optional features applicable to the step C) are therefore applicable to the step e).

Preferably, in the step a), an arch of the patient or a physical model of said arch is scanned while said arch or said physical model of said arch is wearing or not wearing an orthodontic appliance, and in particular while said arch or said physical model of said arch is not wearing an orthodontic appliance.

The updated instant can be different from the reference instant, and in particular be more than 3 days after the reference instant. The method can then be used to view the modifications of the arch between these two instants.

In one embodiment, the virtual dental scene consists of the reference image.

Preferably, in the step d), the nature and/or the location and/or the appearance of an element of the virtual dental scene, and notably of an indicator, is determined as a function:
of the reference image, and/or
of differences between the updated image and the reference image, and/or
of the context.

The reference model can give access to "hidden" information, that is to say information not accessible to the operator or that is difficult to access by the operator. Such hidden information can in particular depend on the reference image, and therefore on the updated image. In one embodiment, at least a part of the hidden information is selected in the step d). The step d) thus makes it possible to create a virtual dental scene which contains such information and the step e) allows it to be presented on the real dental scene or on the representation thereof.

Applications

A method according to the invention can in particular be used for non-therapeutic purposes, in particular for research purposes, for example to assess the efficiency of a treatment or of an orthodontic appliance, or for esthetic purposes, or for teaching purposes.

In one embodiment, the virtual dental scene can relate to the real dental scene as simulated at a simulation instant or, for the past, as observed at a simulation instant. In particular, the virtual dental scene can simulate the real dental scene at the simulation instant. The simulation is preferably obtained by means of a computer, preferably by means of an artificial intelligence algorithm.

The method according to the invention is then particularly useful for an operator, and in particular a patient, to be able to view a dental situation at a prior simulation instant or, preferably, after the updated instant, or view the evolution of such a dental situation by varying the simulation instant.

Preferably, the method comprises a series of cycles of steps A) to C), or c) to e), the virtual dental scene being determined, on each cycle, to simulate a dental situation at the current simulation instant.

In one embodiment, the virtual dental scene is determined by means of a dynamic simulation tool configured to supply at least one element of the virtual dental scene as a function of a determined simulation instant, in particular as a function of a simulation instant after the updated instant.

When it is used for simulation purposes, a method according to the invention can comprise one or more of the following optional features:
the simulation instant is after the updated instant, for example more than 1 day, 10 days or 100 days after the updated instant;
the simulation instant is determined before the step A) or before the step B), preferably by interaction of the operator with a screen;
said screen
is a touch screen and the time interval between the updated instant and the simulation instant is modified by interaction, preferably by dragging, of a finger over said screen, and/or
comprises a field for inputting the simulation instant;
between two cycles of steps A) to C), the time interval between the updated instant and the simulation instant is modified;
the simulation instant is set by modifying the position of a cursor represented on the screen;
in the step B), the nature and/or the location and/or the appearance of an element of the virtual dental scene, and notably of an indicator, is determined as a function:
of the context, and in particular as a function of the distance to another element of the virtual dental scene and/or as a function of a pursued objective, and/or as a function of the simulation instant;
in the step B), a color and/or a form and/or a position of a visible or invisible part of the mouth, preferably of a jaw, of a dental crown and/or of a dental root and/or of the gum of the patient, are determined for the simulation instant, and the virtual dental scene is determined in such a way that it reproduces said color and/or form and/or position;
the patient acquires said updated image in the step A), and observes the screen in the step C).

Such a method according to the invention can in particular be used to simulate:
the effect of one or more orthodontic appliances on the teeth of the patient, notably in order to choose the one best suited to him or her;
the effect of a temporary or permanent stop to a current treatment;
the effect of an application of an instruction.

Notably, the method can be used, notably for teaching purposes, to view the effect of a modification of the frequency and/or of the duration and/or of the technique for brushing of the teeth, or the effect of a delay in changing an orthodontic splint and/or of a delay in making an appointment with the dental care professional.

For example, it can be used to simulate, at the simulation instant, the color and/or the position of the teeth of the patient. Notably, it can be used to view the effect of a treatment for whitening the teeth or the effect of cigarettes.

When the method comprises the steps a) to e), in the step b), the reference model can be modified to simulate the effect of the flow of time between the reference instant and the simulation instant, and in particular the effect of a dental treatment, therapeutic or not, between these instants.

A method according to the invention can even notably be used to:
assess a difference relating to the position and/or the form and/or a dimension of one or more teeth and/or of an orthodontic appliance between the reference instant and the updated instant, or between the simulation instant and the updated instant, notably in the context of an orthodontic treatment, and/or indicate a target location of the dental arch, in particular on one or more teeth.

A method according to the invention can in particular be used to view a stripping undergone by a tooth or a distortion of the gum between the reference and updated instants or between the simulation instant and the updated instant, or guide the placement of an orthodontic appliance or of a part of an orthodontic appliance or of a dental implant or of a decorative item.

In one embodiment, the virtual dental scene relates to the real dental scene, preferably at least partly represents the real dental scene as it appears at the updated instant or as it should appear at the updated instant according to a simulation. In other words, if the virtual dental scene represents the teeth of the patient, it represents them in their position at the updated instant or in their simulated position at the updated instant. The simulation instant is therefore identical or close to the updated instant, for example separated from the updated instant by less than 1 month, less than 2 weeks or less than 1 week.

Device

The invention relates also to a device for implementing a method according to the invention.

Such a device comprises optionally, means for generating and optionally modifying a reference model in the steps a) and b), this means preferably comprising a scanner and a computer;

a camera configured to implement the step A) or c);

a processing unit configured to implement the step B) or the step d);

presentation means configured to implement the step C) or e), and preferably a screen as described previously;

the processing unit, the camera and the presentation means being configured to communicate with one another to implement said steps.

Preferably, the camera is configured so as to acquire a succession of updated images of the real dental scene and transmit said updated images to the processing unit.

Preferably, the processing unit is configured to:

search, for each updated image received from the camera, by observation of a reference model, for a reference image presenting a maximum match with said updated image, determine, as a function of the reference image, a virtual dental scene, and transmit said virtual dental scene to the presentation means;

the presentation means are configured to show the virtual dental scene overlaid on the real dental scene or on the representation of the real dental scene in the updated image.

In one embodiment, the virtual dental scene is presented in transparent mode on the real dental scene or on the representation thereof in the updated image.

In one embodiment, the device comprises glasses in which the camera and the presentation means, preferably the camera, the presentation means and the processing unit, are incorporated.

In one embodiment, the presentation means are configured to present the virtual dental scene on a lens of the glasses, realistically overlaid with the real dental scene or to project the virtual dental scene onto the physical elements which constitute the real scene.

In one embodiment, the device comprises a cellphone or a camera or a laptop computer or a virtual reality headset or a tablet or a mirror, in which the camera and the presentation means, preferably the camera, the presentation means and the processing unit, are incorporated.

The presentation means preferably comprise a screen that makes it possible to display the updated image and present the virtual dental scene on the representation of the real dental scene, in "augmented reality".

The representation of the real dental scene can be an image displayed on the screen of the cellphone or of the camera or of the laptop computer or of the virtual reality headset or of the tablet.

The representation of the real dental scene can be the reflection returned by the mirror.

As will be seen in more detail hereinafter in the description, the observer can thus observe the real dental scene or the representation thereof on the updated image and the virtual dental scene, preferably in transparent mode, on the real dental scene or on the representation thereof on the updated image. He or she can thus immediately have access to the information contained in the virtual dental scene, presented in the environment of the real dental scene. The incorporation of the screen in the glasses is particularly advantageous for this purpose.

Definitions

A "patient" is a person for whom a method according to the invention is implemented, independently of whether or not this person is following a dental treatment.

A "dental situation" defines a set of characteristics relating to an arch of a patient at an instant, for example the position of the teeth, their form, the position of an orthodontic appliance, etc. at that instant.

A "dental care professional" is understood to mean any person qualified to deliver dental services, which includes an orthodontist and a dentist. The operator wearing the glasses is preferably an orthodontist or a dentist.

"Operator" is understood to mean the person who implements the method for the virtual dental scene to be presented to him or her in the step C). The operator can in particular be the patient or the dental care professional.

"Glasses" are understood to mean an appliance which can be worn in front of the eyes of an operator, preferably resting on the nose and/or the ears of the operator.

An "orthodontic appliance" is an appliance worn or intended to be worn by a patient. An orthodontic appliance can be intended for a therapeutic or prophylactic treatment, but also for an esthetic treatment. An orthodontic appliance can be in particular an appliance with arch and attachments, or an orthodontic splint. Such a splint extends in such a way as to follow the successive teeth of the arch to which it is fixed. It defines a generally "U"-shaped channel. The configuration of an orthodontic appliance can be in particular determined to ensure the fixing thereof to the teeth, but also as a function of a target positioning desired for the teeth. More specifically, the form is determined so that, in the service position, the orthodontic appliance exerts strains tending to move the teeth being treated to their target positioning (active orthodontic appliance), or to keep the teeth in this target positioning (passive orthodontic appliance, or "restraining" orthodontic appliance).

"Model" is understood to mean a digital three-dimensional model.

"Image" is understood to mean a two-dimensional image. An image is formed by pixels. The "updated images" are images taken at a so-called "updated" instant. They are preferably extracted from a film taken by a camera. A "reference image" is a view of a "reference" model which presents a maximum match with an updated image.

"Arch" is understood to mean all or part of a dental arch. An "image of an arch", or "model of an arch", is thus understood to mean a representation in two or three dimensions, respectively, of all or part of said arch.

A "scene" consists of a set of elements which can be observed simultaneously. A "dental scene" is a scene comprising an arch.

A "real scene" consists of physical elements. A real dental scene therefore comprises an arch, but also, optionally, an orthodontic appliance worn by the teeth of the arch or manipulated by the operator, and/or a tool manipulated by an operator.

A "virtual scene" consists of representations of elements, notably representations of a physical element of the corresponding real dental scene (that is to say of the real dental scene represented on the updated image from which the virtual dental scene was determined) or of another item of information, or "indicator".

A physical element can be modeled by the reference model, for example a tooth outline, or not modeled by the reference model, for example a tool manipulated by the operator.

A representation of a physical element is not necessarily realistic. For example, a tool can be symbolized by a straight line.

The presentation of a virtual dental scene is "in transparent mode" on a real dental scene when it allows the operator to see, through said virtual dental scene, the real dental scene.

The presentation of a virtual dental scene is "in transparent mode" on an updated image representing a real dental scene when it allows the operator to see the updated image through said virtual dental scene.

A virtual dental scene is displayed "overlaid" or "in register" with a real dental scene or with a representation of a real dental scene on an updated image when it comprises representations of physical elements of the real dental scene which are presented in such a way that the outlines of said representations, possibly transparent, are overlaid on the outlines of said physical elements or of said representations of said physical elements on the updated image, respectively. The overlay thus appears realistic. For example, when the observer observes a tooth of a dental arch, the presentation is determined so that the representation of the tooth on the virtual dental scene is overlaid on the view of that tooth perceived by the operator.

The "location" of an element of the virtual dental scene refers to its position with respect to the elements of the real dental scene or of the representation of these elements on the updated image when the virtual dental scene is presented in the step C).

The "match" (or "fit") between two objects is a measurement of the difference, or "distance", between these two objects.

Preferably, two images or "views" which present a maximum match represent substantially the same elements in the same way. In other words, the representations of the elements on these two images can be substantially overlaid.

"Comprise" or "include" or "present" or "represent" should be interpreted without restriction, unless indicated otherwise.

BRIEF DESCRIPTION OF THE FIGURES

Other features and advantages of the invention will become more apparent on reading the following detailed description and on studying the attached drawing in which:

FIG. 1 represents, schematically, the different steps of an analysis method according to a preferred embodiment of the invention;

FIG. 2 represents an example of a reference image of a reference model;

FIGS. 3 (3a-3b) and 4 (4a and 4b) illustrate the processing of a reference image and of an updated image, respectively, to extract therefrom a reference map and an updated map, respectively, representing outline information;

FIGS. 5, 6 and 7 schematically illustrate examples of devices according to the invention;

FIG. 8 represents the overlay of a virtual dental scene on an updated image.

Figures 6, 7, 8:
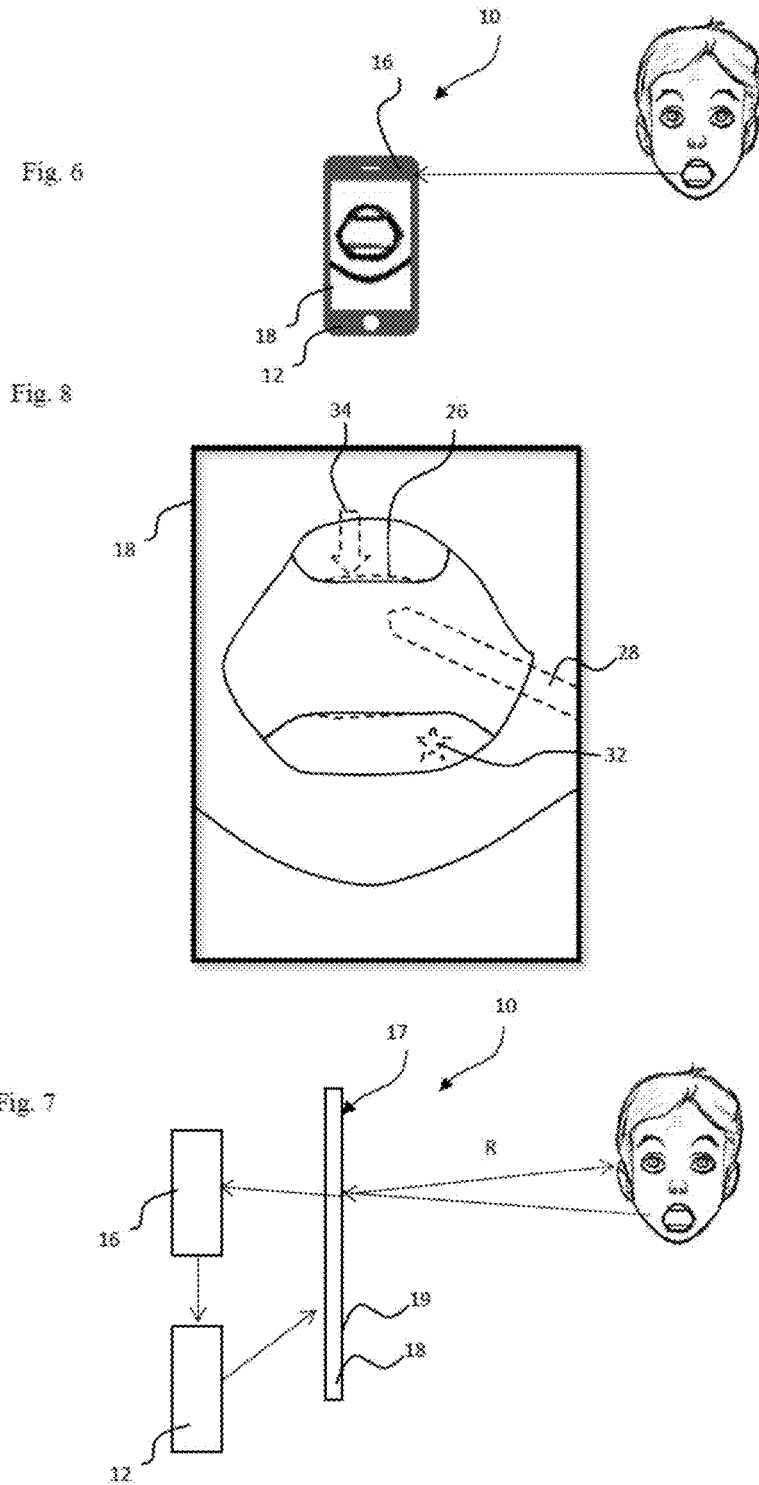

Identical references are used to designate members that are identical or similar in the different figures.

DETAILED DESCRIPTION

Device

A device 10 according to the invention comprises a camera 16, a computer processing unit 12 and presentation means 18. The camera 16, the processing unit 12 and the presentation means are provided with means allowing them to communicate with one another.

As represented in FIGS. 5, 6 and 7, the camera 16 and/or the processing unit 12 and/or the presentation means can be incorporated in glasses conventionally comprising a frame 14 configured to be worn by the nose and the ears of an operator, in a cellphone, in a tablet, in a laptop computer, in a virtual reality headset, in a camera or in a mirror 17.

The camera 16 is intended to acquire updated images representing the real dental scene observed by the operator through the glasses (FIG. 5) or on the screen of a cellphone (FIG. 6) or of a laptop computer, of a virtual reality headset, of a camera or of a tablet, or on the glass 19 of the mirror (FIG. 7). It can be a conventional camera.

In one embodiment, the device comprises means for projecting structured light patterns, for example a cloud of dots, for example laser, in particular infrared. Advantageously, the real dental scene reveals these patterns in a distorted manner, which allows information relating to depth to be deduced therefrom.

In the case where the device comprises a mirror, the glass 19 can be a glass without silvering and the camera can be arranged behind the glass, as in FIG. 7.

In one embodiment, the device comprises several cameras, which makes it possible, by simple trigonometric calculation, to assess the distance between the objects observed and the camera. The multiplicity of the cameras thus makes it possible to speed up the search for the reference images. The cameras thus also make it possible to simulate the three-dimensional view that the observer has of the real dental scene.

"Presentation means" is understood to mean any means configured to receive, from the processing unit 12, a virtual dental scene, and show said virtual dental scene on the real dental scene, on a screen through which an observer can see the real dental scene or on the updated image.

In one embodiment, the presentation means 18 comprise a screen and a projector for projecting the virtual dental scene onto the screen.

Particularly in the embodiment in which the camera is incorporated in glasses, the screen can be transparent. It is preferably fixed to the frame 14, and the virtual dental scene is presented on the screen in order for the operator to see, by observing this screen, not only the real dental scene through the screen, but also the virtual dental scene projected onto the screen.

The glasses conventionally comprise two lenses which extend in front of the two eyes of the operator, respectively, but the number of lenses is not limiting. The lenses can be vision-corrective or not. Several lenses can extend in front of one and the same eye. For example, a first lens can correct the view of the operator and a second lens can be a lens serving as screen.

The HoloLens appliance, developed by the company Microsoft®, is an example of presentation means.

The screen can be opaque and the updated image and the virtual dental scene are presented on the screen, in register, in order for the operator to see, by observing this screen, not only the updated image representing the real dental scene, but also the virtual dental scene.

In this embodiment in particular, the camera can be immobilized with respect to the screen, for example when the camera and the screen are incorporated in a cellphone (FIG. 6) or a laptop computer or a virtual reality headset or a camera or a tablet or a mirror.

Alternatively, the camera can be free (or "independent") with respect to the screen. Advantageously, this latter embodiment allows for great flexibility. For example, in one embodiment, the camera can be introduced into the mouth while the screen remains outside the mouth.

Particularly in the embodiment in which the camera is incorporated in a mirror or is secured to a mirror, the screen can be the reflecting glass 19 of the mirror, and the virtual dental scene can be presented on the screen, in register with the reflection R returned by the glass 19, in order for the operator to see, by observing this screen, not only the reflection R representing the real dental scene, but also the virtual dental scene overlaid on the real dental scene.

The reflection, like the updated image displayed on the screen of the glasses, of the cellphone, of the laptop computer, of the virtual reality headset, of the camera or of the tablet, thus gives the operator a representation of the real dental scene.

The processing unit 12 can comprise the conventional electronic means of any computer, and in particular a central processing unit 22, a program and a memory 24. The memory 24 preferably contains a reference model of at least a part of the real dental scene, and in particular a model of the dental arch, for example as represented in FIG. 2. The program comprises code instructions that make it possible, when they are executed, to implement the step d), and in particular to analyze an updated image, to search for a view of the reference model which presents a maximum match with the updated image, that is to say a reference image, then to determine, accordingly, a virtual dental scene.

In one embodiment, the device also comprises an interface allowing an operator to parameterize the virtual dental scene. Preferably, the interface is configured for an operator to be able to modify a simulation instant determining the virtual dental scene. The content of the virtual dental scene can in particular consist of the representation of elements of the real dental scene under an appearance and/or at a position that are simulated for the past or future simulation instant or known at a past simulation instant.

For example, in one embodiment, the screen is a touch screen and the operator can modify the simulation instant by entering a date in an input field or by moving one or more fingers over the screen. For example, a movement to the right of the screen can result in an advance to the future and a movement to the left of the screen can result in a movement back to the past. The virtual dental scene presented is adapted accordingly, preferably in real time.

The interface can also be a mechanical member, for example a button or a thumbwheel.

In one embodiment, the device is configured for the time interval between the updated instant and the simulation instant to change continually from one cycle to another, that is to say for the succession of cycles of steps A) to C) or c) to e) to simulate an advance in time or a return in time. In one embodiment, the time difference between two successive simulation instants is constant, which makes it possible to view a change in which the time flows at a constant speed.

The processing unit determines the conditions in which the virtual dental scene must be presented to appear, to the operator, overlaid with the real dental scene.

When the virtual dental scene has to be presented on the updated image displayed on a screen, the operator observes the screen and therefore sees what is observed by the camera. Simple operations, such as scaling, a correction of the perspective effects or a realignment on the updated image, can be sufficient to ensure a realistic overlay of the virtual dental scene on the updated image, for example by using characteristic marks, as described hereinbelow.

When the virtual dental scene has to be presented on a transparent screen through which an operator observes the real dental scene, it is preferable for the camera to be arranged so as to capture an updated image which corresponds to the view of the real dental scene by the observer. It is also preferable for the screen to be at a constant distance, and oriented in a fixed manner with respect to the observer. Advantageously, the processing unit can thus easily determine, from the updated image acquired by the camera, the view of the real dental scene observed by the operator, and the conditions in which the virtual dental scene must be presented to appear, to the operator, overlaid with the real dental scene.

Method

A method according to the invention can be implemented by means of a device according to the invention.

In the step a), at a reference instant, a reference model is generated, preferably by means of a scanner.

The reference model can be a model of the arch of the patient or be composed of a model of this arch and of a model of an orthodontic appliance arranged on said model of the arch.

The creation of the reference model results preferably from the taking of measurements.

Preferably, an arch of the patient is scanned with a 3D scanner, optionally while the patient is wearing an orthodontic appliance, or a molding of this arch, so as to create a reference model. Preferably, the scan is performed with a conventional 3D scanner.

The reference model obtained by means of a scanner represents an arch, but also, if necessary, any object scanned at the same time as the arch, for example an orthodontic appliance or a decorative item fixed to the arch.

The reference model can alternatively be a generic arch model, chosen from a base of generic models, that is to say an arch model that is applicable, roughly, to several patients, or result from a distortion of such a generic model. The distortion can in particular be as a function of measurements or of observations made on the patient, for example as a function of photos of his or her dental arches. The distortion of a model in order for it to be able to correspond to one or more photos can implement a metaheuristic method, as described notably in WO 2016/066651.

A generic arch model can in particular be a model obtained by a statistical processing, for example an average, over more than 5, more than 10, more than 100 or more than 1000 historical models generated by means of a scanner. The historical models are preferably models of dental arches of "historical" patients having dental characteristics identical or similar to those of the patient for whom the reference model is being generated, for example who have suffered the same pathology and/or have the same age and/or have the same sex and/or have a similar morphology.

The reference model, three-dimensional, can be observed from any angle. An observation of the model, from an angle and at a distance that are determined, is a "view of the model". FIGS. 2 and 3a are examples of views of a reference model.

The views of the reference model are intended to be compared with the updated images in order to determine, for each updated image, a reference image that most closely resembles the updated image, then consequently construct a virtual dental scene adding information relating to the elements represented on the updated image.

The reference instant can be close to the updated instant, for example separated (after or before) by less than 1 month, 2 weeks or 1 week or 3 days from the updated instant. Updated images can then be used to distort a generic model until the reference model corresponding to the dental situation at the updated instant is obtained. Moreover, the virtual dental scene then provides information on the dental situation specific to the updated instant. For example, if the reference model models the roots of the teeth, the virtual dental scene can represent the roots of the teeth.

The reference instant can be separated from the updated instant, for example separated by more than 1 month, 2 weeks or 1 week or 3 days from the updated instant. The reference model can then differ substantially from the reality at the updated instant. The information supplied by the virtual dental scene can then relate to the change to the dental situation between the reference instant and the updated instant. For example, they can provide information on a movement of the teeth or of an orthodontic appliance.

For example, the method can be used to check whether a passive restraining appliance correctly holds the teeth in position after a dental treatment. The reference model can be generated immediately after the fitting of the appliance and the acquisition of an updated image can take place one month after this fitting. The reference image and the virtual dental scene will therefore concern the teeth in their position at the end of treatment and the presentation of the virtual dental scene on the real dental scene, at the updated instant, will thus allow the dental care professional to detect the differences with their real positions.

In the step b), in one embodiment, the reference model is modified.

The modification can be performed at any moment between the reference instant and the updated instant. Preferably, it is performed substantially at the reference instant.

The modification of the reference model can be a distortion of this model.

In one embodiment, the reference model is segmented, and in particular tooth models are created, as described in WO 2016/066651. Then, the tooth models are moved or distorted.

The modification in the step b) can simulate the effect of the flow of time, for example the effect of a dental treatment, between the reference instant and the updated instant. The modification of the reference model thus results in a model representing the teeth in a position or a form estimated for the updated instant.

The movement or the distortion of the tooth models can also be determined or refined on the basis of one or more updated images, as described in WO 2016/066651. Preferably, the initial reference model, determined in the step a), then results from measurements by means of a scan of at least one arch or of at least one molding of an arch.

The method can thus be used to check whether the progress of a dental treatment is as predicted, the initial reference model being modified to correspond to the situation anticipated at the updated instant. In orthodontics, substantial changes can take a few days. Preferably, in this embodiment, the time interval between the updated instant and the reference instant is greater than 3 days, even greater than 1 week, greater than 2 weeks, greater than 4 weeks, greater than 8 weeks, greater than 12 weeks, even greater than 16 weeks.

The reference image, resulting from an observation of the modified reference model, then reveals the teeth in their positions or forms anticipated at the updated instant. It constitutes or can be incorporated in a virtual dental scene whose presentation, in the step e), allows the dental care professional to detect the differences between the real positions or forms of the teeth and the positions or forms anticipated for the updated instant.

The modification of the initial reference model can consist of an addition of another model and/or of the modification of this other model. For example, a model of an orthodontic appliance fitted onto the arch can be added to a reference model which might initially represent only the arch. The modification of the reference model can then include a modification of this orthodontic appliance for it to appear in its position or form anticipated for the updated instant. The presentation thereof, in the step e), then allows the dental care professional to detect the differences between the real position or form of the orthodontic appliance and the position or form anticipated for the updated instant, and notably to detect any separation of an attachment.

In the step c), at the updated instant, an updated image is acquired with the camera that represents a real dental scene. In the figures, the updated image is represented by a continuous line on the screen 18.

A device according to the invention in which the camera is fixed onto the frame of glasses or is incorporated in a mirror makes it possible to acquire an updated image which represents with great accuracy the real dental scene observed by the operator through the lenses of these glasses or on this mirror.

A device according to the invention in which the camera is incorporated in a cellphone, a laptop computer, a tablet or a camera makes it possible to acquire an updated image which exactly represents the real dental scene observed by the operator on the screen of the cellphone, of the computer, of the tablet, or of the camera, respectively.

With a virtual reality headset in particular, the camera can be rigidly secured to or be independent of the screen. The independence of the camera and of the screen advantageously allows the operator to operate without directly seeing the real dental scene, that is to say by seeing it only on the screen. He or she can thus work "blind".

Preferably, the updated image is in color, preferably in real colors.

In the step d), a reference image is sought which presents a maximum match with the updated image.

In the step d), all the known methods for producing a maximum match can be envisaged.

A maximum match can be obtained notably as a result of an optimization so as to minimize said distance ("best fit").

Preferably, the reference image is sought by observing the reference model from different observation angles and different distances, until a view of the reference model is obtained which corresponds substantially to the updated image, that is to say which can be substantially overlaid on it. For each updated image, a reference image is thus obtained that presents a maximum match with the updated image. This search is preferably performed by means of a metaheuristic method, preferably evolutionist, preferably by simulated annealing.

The metaheuristic methods are known optimization methods. They are preferably chosen from the group formed by the evolutionist algorithms, preferably chosen from among: evolution strategies, genetic algorithms, differential evolution algorithms, distribution estimation algorithms, artificial immune systems, path recomposition, shuffled complex evolution, simulated annealing, ant colony algorithms, particle swarm optimization algorithms, tabu search, and the GRASP method;

the kangaroo algorithm, the Fletcher and Powell method, the sound effects method, stochastic tunneling, random restart hill climbing, the cross-entropy method, and hybrid methods of the metaheuristic methods cited above.

The exploration of the reference model to search for the reference image can comprise one or more of the features of the steps c), d) and e) of WO 2016/066651, in as much as they relate to such exploration.

Preferably, the updated image is processed to produce an updated map representing, at least partially, discriminating information, and said search comprises the following steps:

i) acquisition of a view of the reference model;

ii) processing of the view to produce at least one reference map representing, at least partially, the discriminating information;

iii) comparison of the updated and reference maps so as to determine a distance between said updated and reference maps and, if the distance is greater than a threshold, modification of the view, then return to the step ii).

The updated and reference maps represent the same discriminating information. The discriminating information is characteristic information which can be extracted from an image ("image feature"), conventionally by computer processing of this image. It is preferably chosen from the group consisting of outline information, color information, density information, distance information, brightness information, saturation information, information on glare and combinations of such information.

The person skilled in the art knows how to process an image to reveal the discriminating information, and therefore create the corresponding map.

For example, FIG. 4b is an updated map relating to the outline of the teeth obtained from the updated image of FIG. 4a. FIG. 3b is a reference map relating to the outline of the teeth obtained from the view of FIG. 3a.

The modification of the view is preferably guided by heuristic rules, for example by favoring the modifications which, according to an analysis of the preceding distances, appear the most favorable to reduce it.

The step iii) culminates in a reference image that can substantially be overlaid on the updated image.

A maximum match between the reference image and the updated image can be obtained also as a result of the overlaying of identified markers on these two images, for example the overlaying of fixed markers like the end of a tooth or a point of contact between two teeth.

The virtual dental scene preferably comprises, or consists of, the reference image. The reference image is a particular example of a virtual dental scene.

In FIG. 8, the elements of the virtual dental scene are represented by dotted lines.

In a preferred embodiment, a virtual dental scene comprises a representation, preferably realistic, of one or more elements of the corresponding real dental scene. In particular, preferably, it comprises a representation of the arch, but also optionally, for example, a representation of an orthodontic appliance worn by the teeth of the arch or that the operator manipulates in front of the arch, or of a tool that the operator manipulates in front of the arch.

As represented in FIG. 8, the virtual dental scene can for example represent the outlines 26 of the teeth and its projection onto the teeth can facilitate the detection of movements or of distortions of the teeth.

The virtual dental scene can also comprise the representation of one or more physical elements of the real dental scene not modeled by the reference model, for example a tool 28 manipulated by the operator. To identify such physical elements, the updated image is analyzed, for example by means of artificial intelligence algorithms.

The virtual dental scene can also comprise the representation of one or more physical elements which are not in the real dental scene, for example a tool or an orthodontic appliance or a decorative item 32, for example positioned on the virtual dental scene so as to appear, on the real dental scene, at a location ("target placement") where the tool or the orthodontic appliance or the decorative item, respectively, ought to be arranged by the dental care professional or by the patient.

The representation of a physical element can be realistic, for example consist of the outlines of the physical element considered, or symbolic. For example, the bit of a drill can be symbolized by an arrow.

The representation of the physical elements of the virtual dental scene can be two-dimensional and/or three-dimensional. The presentation of the virtual dental scene can be in particular a hologram.

The virtual dental scene can also comprise, in addition or alternatively to the representation of physical elements, for example of the reference image, one or more indicators 34.

An indicator is an element of a virtual dental scene which does not represent, even symbolically, a physical element of the real dental scene.

An indicator can in particular be a text or a symbol (a dot, a line, an arrow, a color control patch, etc.), for example a symbol illustrating differences between the updated image and the reference image, or that provides information relating to a deed performed by the operator, for example indicating to him or her a direction for a tool that he or she is manipulating.

In one embodiment, the indicator points to a location to which the operator must pay particular attention, for example a brushing. The indicator can be an image, preferably playful, for example a drawing of a monster or of a microbe, to which the operator must apply a tool, for example a toothbrush. Such an indicator improves the learning of brushing of teeth, for example.

In FIG. 8, the indicator 34 points to a dental region which has been abraded.

The nature of an indicator can be determined as a function of the reference image. The indicators can in particular be associated with the reference model or with a region of the reference model. They are for example stored in a database in the memory 24 of the processing unit.

For example, additional information can be associated with different regions of the reference model, for example to indicate decay, brittle zones, or bonding zones for an orthodontic appliance. Additional information can also be associated with the reference model as a whole, for example to specify the circumstances of its production or information on the patient or on the orthodontic appliance possibly represented. The indicators make it possible to present such additional information.

The nature of an indicator can be determined as a function of the differences between the updated image and the reference image.

For example, indicators can be added to reveal a distortion or a movement of a tooth, or a detachment of an orthodontic appliance.

The nature and/or the location and/or the appearance of an indicator can be determined as a function of the context, and in particular as a function of the distance to another element of the virtual dental scene and/or as a function of a pursued objective. For example, it will appear with an appearance that is a function of the distance to a particular tooth or a function of the risk for the patient.

The context is defined by the conditions in which the method is used.

For example, the operator can have the objective of checking the positioning of the orthodontic appliance worn by the patient. The indicators which are not linked to this check, for example the indication of the zones of decay, are not then necessary.

In one embodiment, before the step d), the operator inputs additional information into the database, as a function of the use of the targeted method. For example, he or she specifies a location for attaching a decorative item or for milling a tooth. The corresponding indicators can advantageously be added to the virtual dental scene.

For example, an arrow can point to a zone of a tooth in order to indicate to the operator the point where an orthodontic appliance or a decorative item must be fixed, or on which he or she needs to act, for example by means of a tool such as a burr.

An indicator can also represent, realistically or not, a non-visible part of a physical element of the real dental scene (and which, not being visible to the operator, therefore does not belong to the real dental scene), for example a root of a tooth, a bone or a dental nerve.

The elements which make up the virtual dental scene are positioned in this scene as a function of the elements of the real dental scene, and therefore, in this particular case, as a function of the reference image. In particular, the representations of real physical elements are preferably positioned in the virtual dental scene so that, in the step e), they are overlaid, accurately, with these real physical elements or with their representations on the updated image.

Likewise, an indicator adding specific information to a physical element, for example specific to a tooth, is preferably positioned so that, in the step e), it appears in immediate proximity to or overlaid on this physical element, for example on this tooth.

Indicators can be arranged so as to be displayed, in the next step, at the points where differences have been identified between the reference image and the updated image. For example, a red mark can be displayed at the locations where an orthodontic appliance has come unstuck from the teeth.

In one embodiment, the context is changing and the nature and/or the location, in the virtual dental scene, of the indicators are adapted accordingly. In particular, the nature and/or the location of the indicators can be determined as a function of the nature and/or of the location of indicators displayed in prior virtual dental scenes, that is to say scenes determined in preceding cycles c)-e) (or A) to C)), and/or as a function of the time interval with said prior virtual dental scenes, and/or as a function of differences between the updated images of successive cycles c)-e) (or A) to C)).

For example, the method can be used to guide an action of the operator with a tool, for example drilling by means of a drill. An element of the virtual dental scene can be an arrow indicating the orientation of the drill and the position of its free end. The database can contain a protocol setting, for example, the point of penetration into the tooth, the trajectory and the optimal speed of advance of the drill. On each cycle of the steps c) to e) (or A) to C)), the location of the element in the virtual dental scene is then determined as a function of its location in the virtual dental scenes determined previously and, preferably, as a function of the time interval between said virtual dental scene and said prior virtual dental scenes.

Also preferably, the tool, for example the drill, which appears on the successive updated images, is identified on these images and the location of the element in the virtual dental scene is adapted to take account of the real position of the tool. Advantageously, the representation of the indicator in the virtual dental scene can therefore change as a function of the real position of the tool. Notably, it can thus be adapted to the actual rate of progress or to the actual trajectory of the tool.

In one embodiment, the appearance of an element of the virtual dental scene changes as a function of the context.

For example, an element of the virtual dental scene is identified which does not comply with an assessment criterion, for example because it exceeds a risk threshold, then attention is drawn to this element in the virtual dental scene. For example, the color of the element can be modified if the analysis of the context shows that the situation is becoming dangerous, for example because the tool is not following the desired trajectory or because the orthodontic appliance would result in an excessive correction of the positioning of the teeth.

In one embodiment, the virtual dental scene does not include the reference image. The reference image can be used to determine the nature and/or the location of the elements in the virtual dental scene. However, it is not presented to the observer in the step e) (or C)).

In one embodiment, the virtual dental scene is determined as a function of a past or future simulation instant. In particular, it can comprise a representation, preferably realistic, of one or more elements of the corresponding real dental scene in a past or future configuration.

In one embodiment, it comprises a representation of the arch and/or a representation of an orthodontic appliance worn by the teeth of the arch as measured or simulated at a past simulation instant.

In one embodiment, it comprises a representation of the arch and/or a representation of an orthodontic appliance worn by the teeth of the arch as anticipated for a future simulation instant.

The simulation at a past or future simulation instant can be performed by any simulation software or by an operator, for example by a dental care professional.

The virtual dental scene can for example represent the outlines of the teeth, the positioning of an orthodontic appliance or the color of the teeth at the simulation instant. The presentation of the virtual dental scene on the real dental scene, preferably in transparent mode on the real dental scene, thus allows the change between the updated instant and the simulation instant to be easily detected.

When an indicator represents a non-visible part of a physical element of the real dental scene, for example a root of a tooth, the information relating to this indicator is preferably included in the reference model. For example, the reference model can be a model of the dental arch in which the crowns of the teeth, but also the roots of the teeth, are modeled, for example by means of a cone beam scanner. The method according to the invention thus allows the operator to view parts of the dental arch of the patient which are not visible on the real dental scene. Advantageously, these non-visible parts are represented in their real relative position with respect to the physical elements of the real dental scene. For example, the operator sees the roots and the nerves of the teeth that he or she observes in the mouth of the patient. He or she can thus avoid an interaction with a tool that he or she is manipulating or adapt an orthodontic appliance to limit the risk of a collision between the roots of adjacent teeth, and therefore limit the risk of root resorption. For example, in an injection by means of a syringe, the operator can accurately introduce the needle, to reach a dental root, without touching a dental nerve. The pains felt by the patient are thereby limited.

In the step e), the virtual dental scene is presented, as a function of the reference image, overlaid on the real dental scene or on the representation of the real dental scene in the updated image.

The virtual dental scene can be directly projected onto the real dental scene. For example, red light spots can be projected onto the teeth to identify bonding zones for orthodontic attachments.

The virtual dental scene can be displayed on a screen.

When the screen is transparent, in particular in the embodiment in which it is incorporated in glasses, the operator can thus observe the virtual dental scene on the screen and the real dental scene through the screen, in transparent mode behind the virtual dental scene.

When the screen is opaque, particularly in the embodiment in which the screen is the screen of a cellphone, of a laptop computer, of a virtual reality headset or of a tablet, the operator can thus simultaneously observe the updated image and the virtual dental scene on the screen.

The virtual dental scene can be sufficiently transparent to reveal the real dental scene or the updated image under it.

Alternatively, the virtual dental scene can be opaque, so as not to reveal the real dental scene or the updated image which extends behind or under it. The opacity of the virtual dental scene is particularly advantageous for simulating a past or future dental situation, for example for viewing the whitening of the teeth under the effect of a treatment for that purpose, or the movement of a tooth, for example under the effect of an orthodontic treatment or in the absence of an orthodontic treatment, for example to view periodontoclasia of a tooth. When the virtual dental scene is presented on the updated image, it can be added on top of the updated image or, in an equivalent manner, the updated image can be replaced by an image reprocessed by computer to reveal the virtual dental scene.

"Presentation of the virtual dental scene overlaid on the representation of the real dental scene in the updated image" should therefore be understood to include any presentation showing the virtual dental scene on the representation of the real dental scene, including the display of a reprocessed image.

When the screen is the glass of a mirror, the operator can simultaneously observe, on the screen, his or her reflection and the virtual dental scene, overlaid on his or her reflection. In particular, the patient can view the effect of a dental treatment, therapeutic or not.

The virtual dental scene is presented as a function of the reference image and therefore, indirectly, as a function of the updated image. In particular, it is positioned, or "framed", with respect to the real dental scene as a function of the reference image.

The virtual dental scene is presented overlaid, or "in register", with the real dental scene or with the representation thereof on the updated image, which facilitates the comparison. In other words, the elements of the virtual dental scene which correspond to elements of the real dental scene are substantially exactly overlaid on the latter or on the representations of the latter. Notably when the virtual dental scene is presented in transparent mode, the differences between the real dental scene or the representation thereof on the one hand and the virtual dental scene on the other hand thus appear clearly to the operator. The indicators also present to him or her information facilitating analysis of the situation.

Preferably, to present the virtual dental scene in register on the real dental scene or on the representation thereof on the updated image, characteristic marks are identified on the updated image whose position with respect to the virtual dental scene is known. For example, ends of teeth or characteristic forms of teeth are identified that are represented both on the updated image and on the virtual dental scene. The reference image from which the virtual dental scene was determined can in particular be used to identify the position of the characteristic marks in the virtual scene. In the step e) (or C)), the representations of these characteristic marks are then overlaid on the updated image and in the virtual dental scene, which allows the virtual dental scene to be accurately positioned with respect to the characteristic marks represented on the updated image.

Preferably, the method then returns to the step c) (or A)), preferably less than 30 seconds, less than 10 seconds, less than 5 seconds, preferably less than 3 seconds, preferably less than 1 s, less than 0.5 s, less than 0.2 s, preferably less than 0.1 s after the step e) (or C)). Preferably, the cycle of the steps c) to e) (or A) to C)) is performed in real time, uninterrupted.

Alternatively, in one embodiment, the method is completed at the end of the step e) (or C)), without returning to the step c) (or A)). The method is thus performed "on demand", and not in real time.

Application Examples

Real Time Assistance in an Intervention on the Teeth

Notably when the image acquisition appliance is in the form of glasses, the invention can be used in an intervention on the teeth, by the dental care professional wearing the glasses.

In one embodiment, the method is used in the context of an operation of stripping of a tooth, or of milling. Preferably, the virtual dental scene represents the tooth in its final form, after the stripping or the milling to be performed. Preferably, the dental care professional sees the outline of the tooth in its final form accurately overlaid, that is to say in register, on the real tooth. This information allows him or her to machine the tooth with perfect accuracy.

In one embodiment, the method is used to fix a dental attachment, or "bracket", to a tooth. Preferably, the virtual dental scene represents the attachment in its final position, after it has been fixed onto the tooth. Preferably, the dental care professional sees the virtual outline of the attachment in its final position with respect to the real tooth. This information allows him or her to place the real attachment precisely overlaid with the attachment of the virtual dental scene, and therefore position it on the real tooth with perfect accuracy.

The method can also be used to fix a decorative item to the teeth.

In the intervention, the invention allows the operator, in particular a dental care professional, to access relevant information. Such information is presented to him or her, preferably in real time, overlaid with the real dental scene that he or she observes directly or on the updated image. The invention thus makes it possible to considerably increase the quality of the analysis of the situation, and, if necessary, adapt an intervention accordingly.

Improving Observance and Use for Teaching Purposes

In one embodiment, the method is used to obtain a better acceptance of the treatment by the patient. In particular, it can be used to simulate, realistically, a dental treatment. Preferably, the image acquisition appliance is then a cell-phone, a laptop computer, a tablet or a mirror.

With a cellphone, a laptop computer or a tablet, the patient films the dental arches, as if taking a selfie. With a mirror, the patient is preferably filmed through the surface of the mirror, which allows the updated image to faithfully represent the reflection R observed by the patient.

Overlaid with the updated images which follow one another on the screen of the telephone, of the computer or of the tablet, or overlaid with his or her reflection on the mirror, the patient sees corresponding virtual dental scenes, which represent a step of the dental treatment at a simulation instant. For example, the simulation instant can be the instant marking the start of the treatment and the virtual dental scene can represent an orthodontic appliance that the patient is considering wearing. The patient can then view his or her face after the orthodontic appliance has been put in position in his or her mouth. By turning the head or by moving the cellphone, the laptop computer or the tablet, or by moving in front of the mirror, he or she can easily modify the direction of observation, the virtual dental scene being adapted in real time.

Preferably, the patient can modify the simulation instant by interaction with the screen, for example by moving a virtual cursor. The virtual dental scene is adapted accordingly, notably to take account of the effect of the treatment. By acting on the cursor, the patient can then simulate the progress of the treatment, that is to say view, for example, how the teeth will be moved and/or change color, notably in the case of a teeth whitening treatment or if the teeth are subject to a coloring agent, for example if the patient smokes or drinks large quantities of tea or of coffee. The movement of the cursor thus allows him or her to simulate an acceleration of time.

This simulation facilitates the decision-making by the patient and advantageously constitutes an incentive to follow the treatment.

In one embodiment, the patient can modify the value of other parameters of the simulation. For example, he or she can modify treatment parameter values.

For example, he or she can simulate the effect of one or more orthodontic appliances, notably in order to choose the one that best suits him or her;

the effect of a temporary or permanent stop to a current treatment;

the effect of more or less strict observance of the instructions received, notably to view the effect of a modification of the frequency and/or of the duration and/or of the technique for brushing the teeth, or the effect of a delay in changing an orthodontic splint and/or of a delay in making an appointment with the dental care professional.

He or she can thus simulate the effect of poor observance of the medical prescription, which is a factor in improving observance.

In one embodiment, the virtual dental scene shows warnings, preferably in the form of a message or of a highlighting of an element of the virtual dental scene, for example by showing in red a zone which should be brushed more carefully.

Generally, the invention can be used to assess the dental situation of the patient, notably to check the progress of a dental treatment, and/or, outside of the context of a dental treatment, to check a change of color and/or of form and/or of the arrangement of the teeth or of the gums.

Analysis of a Changing Dental Situation

In one embodiment, the method is used to view the stripping undergone by a tooth, for example through bruxism. Preferably, the virtual dental scene represents the tooth in its prior form, before the stripping. Preferably, the operator, generally the patient or the dental care professional, sees the outline of the tooth in its prior form overlaid on the real tooth or on the representation thereof on the updated image. This information allows him or her to immediately and accurately view the scale of this wear, notably when the virtual dental scene is presented in transparent mode.

In one embodiment, the method is used to view a distortion of the gum, and in particular a recession of the gum. Preferably, the virtual dental scene represents the gum in its initial form, before the distortion thereof. Thus, the operator, generally the patient or the dental care professional, sees the outline of the gum in its initial form overlaid on the real gum or on the representation thereof. This information allows him or her to immediately and accurately view this distortion, notably when the virtual dental scene is presented in transparent mode.

Of course, the invention is not limited to the embodiments described above and represented.

In particular, the patient is not limited to a human being. A method according to the invention can be used for another animal.

The invention is not limited to a method comprising steps a) to e). In particular, the search for a reference image is not essential to the implementation of the invention. If a reference image is not available, the elements which make up the virtual dental scene can be positioned on the real dental scene or the representation thereof, as a function of the updated image.

A virtual dental scene can be determined as a function of several reference images obtained from several respective updated images acquired simultaneously or at different, for example successive, updated instants.

The invention claimed is:

1. A method for analyzing a real dental situation of a patient, the method comprising the following successive steps:

A) at an updated instant, acquisition of an updated image representing a real dental scene as observed by an operator;

B) simulation, for a simulation instant, of the real dental scene represented on the updated image, then determination of a virtual dental scene as a function of said simulation, the simulation being obtained by means of an artificial intelligence algorithm, the virtual dental scene being determined as a function of a value of at least one treatment parameter that can be modified by an operator, the treatment parameter relating to the wearing of an orthodontic appliance by the patient and/or to the observance of a treatment instruction by the patient;

C) presentation of the virtual dental scene in transparent mode and overlaid on the real dental scene, or display of the updated image on a screen and presentation of the virtual dental scene overlaid with the representation of the real dental scene on the updated image displayed on the screen, in transparent mode or not on said representation;

a step A) being repeated less than five seconds after the step C);

wherein, between two cycles of steps A) to C), a time interval between the updated instant and the simulation instant is modified; and wherein the virtual dental scene represents the real dental scene at a past or a future simulation instant, or as it should appear at the updated instant according to the simulation.

2. The method as claimed in claim 1, wherein the simulation instant is separated from the updated instant by more than three days.

3. The method as claimed in claim 1, wherein the screen is a touchscreen and the time interval between the updated instant and the simulation instant is modified by interaction with the screen, preferably by dragging a finger over said screen, and/or comprises a field for inputting the simulation instant.

4. The method as claimed in claim 1, wherein a camera is used in the step A) and wherein the camera and/or the screen are incorporated in a cellphone, a laptop computer, a virtual reality headset, a tablet, a camera or a mirror, the glass of the mirror, preferably without silvering, constituting said screen, or wherein the screen and the camera are independent of one another, that is to say are not rigidly secured to one another.

5. The method as claimed in claim 1, wherein, in the step B), a color and/or a form and/or a dimension and/or a position of a visible or invisible part of the mouth, preferably of a jaw, of a dental crown and/or of a dental root and/or of the gum of the patient, are determined for the simulation instant, and the virtual dental scene is determined in such a way that it reproduces said color and/or form and/or position.

6. The method as claimed in claim 1, wherein, in the step B), an element of the virtual dental scene is identified which does not observe an assessment criterion, and this element is highlighted in the virtual dental scene and/or a message relating to the said element, preferably an instruction to be followed by the patient, is added to the virtual dental scene.

7. The method as claimed in claim 6, wherein the assessment criterion relates to the state of health of the patient and/or to the positioning of an orthodontic appliance worn by the patient and/or to the condition of an orthodontic appliance worn by the patient and/or to a cost for a dental treatment.

8. The method as claimed in claim 1, comprising the following successive steps:

a) at a reference instant, generation of a reference model digitally modelling at least one arch of the patient;

b) optionally, modification of the reference model;

c) at the updated instant, acquisition of said updated image, according to the step A);

d) search, by observation of the reference model, optionally modified, for a reference image exhibiting a maximum match with the updated image, then determination, as a function of the reference image, of the virtual dental scene, according to the step B);

e) presentation of the virtual dental scene according to the step C).

9. The method as claimed in claim 8, wherein, in the step a), the reference model is generated by scanning an arch of the patient or a physical model of said arch or by choosing a generic arch model from a database of generic models, then by distorting said generic model as a function of measurements or of observations made on the patient.

10. The method as claimed in claim 8, wherein, in the step b), the reference model is modified to simulate the effect of the flow of time between the reference instant and the simulation instant.

11. The use of a method as claimed in claim 1 to simulate:

the effect of one or more orthodontic appliances; or the effect of a temporary or permanent stop to a current treatment, therapeutic or not; or the effect of a future treatment, therapeutic or not, preferably to modify the color or the position of the teeth; or the effect of the application of an instruction.

12. The use as claimed in claim 11, to view the effect of a modification of the frequency and/or of the duration and/or of the technique for brushing of the teeth, or the effect of a delay in changing an orthodontic splint and/or of a delay in making an appointment with the dental care professional.

* * * * *